United States Patent
Siegel et al.

(10) Patent No.: US 9,169,193 B2
(45) Date of Patent: Oct. 27, 2015

(54) METHOD FOR PRODUCING O-ALKYLATED AMINOALCOHOLS

(75) Inventors: Wolfgang Siegel, Limburgerhof (DE); Gerd Haderlein, Grünstadt (DE); Tobias Stäb, Mannheim (DE)

(73) Assignee: BASF SE (DE)

( * ) Notice: Subject to any disclaimer, the term of this patent is extended or adjusted under 35 U.S.C. 154(b) by 1165 days.

(21) Appl. No.: 12/158,517

(22) PCT Filed: Dec. 11, 2006

(86) PCT No.: PCT/EP2006/069528
§ 371 (c)(1),
(2), (4) Date: Jun. 20, 2008

(87) PCT Pub. No.: WO2007/074046
PCT Pub. Date: Jul. 5, 2007

(65) Prior Publication Data
US 2011/0144390 A1    Jun. 16, 2011

(30) Foreign Application Priority Data

Dec. 22, 2005 (EP) ..................................... 05112826

(51) Int. Cl.
*C07C 215/00* (2006.01)
*C07C 213/06* (2006.01)

(52) U.S. Cl.
CPC ........... *C07C 213/06* (2013.01); *C07C 2101/14* (2013.01)

(58) Field of Classification Search
CPC ...................................................... C07C 213/06
See application file for complete search history.

(56) References Cited

FOREIGN PATENT DOCUMENTS

DE    103 44 447        5/2005
JP    2009520750 A      5/2009

OTHER PUBLICATIONS

Khabnadideh et al. Bioorganic & Medicinal Chemistry Letters 13 (2003) 2863-2865.*
Sergio et al. Journal of Polymer Science Part A: Polymer Chemistry, vol. 44, Issue 2, 2006, 983-992.*
Deshayes et al. Tetrahedron 55 (1999) 10851-10870.*
Chem and Pharma Bulletin, 1985, vol. 33, pp. 1140-1147, Nishi.
Organikum, 1986, pp. 191 ff.
Journal Org Chem, 1977, vol. 42, pp. 377-378, Whitesell.
Journal Med Pharm Chem, 1961, vol. 3, pp. 409-417, Surrey and Mayer.
Journal Org Chem, 1978, vol. 43, pp. 892-898, Meyers.
Synthetic Communications, 1995, vol. 25, pp. 907-913, Hu.

* cited by examiner

*Primary Examiner* — Clinton Brooks
(74) *Attorney, Agent, or Firm* — Drinker Biddle & Reath LLP

(57) ABSTRACT

A process for preparing O-alkylated amino alcohols by reacting N-unsubstituted or N-monosubstituted amino alkoxide salts with alkyl halides, the amino alkoxide salts being formed by means of alkali metal or alkaline earth metal hydroxides.

10 Claims, No Drawings

METHOD FOR PRODUCING O-ALKYLATED AMINOALCOHOLS

CROSS REFERENCE TO RELATED APPLICATIONS

This application is a National Phase filing under 35 U.S.C. § 371 of PCT/EP2006/069528 filed Dec. 11, 2006, which claims priority to patent application No. 05112826.2, filed in Europe on Dec. 22, 2005. The entire contents of each of the above-applications are incorporated herein by reference.

STATE OF THE ART

The present invention is directed to a process for preparing N-unsubstituted and N-monosubstituted amino alkyl ethers or amino benzyl ethers. In particular, the invention is concerned with the regioselective O-alkylation or O-benzylation of N-unsubstituted and N-monosubstituted amino alcohols. Such amino alkyl ethers and amino benzyl ethers are valuable intermediates for the preparation of bioactive ingredients (EP 0691346; T. Nishi et al. Chem. Pharm. Bull. 1985, 33(3), 1140-1147; D. Lewis et al. Steroids, 1995, 60, 475-483; D. Kikelj et al. J. Med. Chem. 1998, 41, 530-539; M. G. N. Russell et al., J. Med. Chem. 1999, 42, 4981-5001; Fray et al. Bioorg. Med. Chem. Lett. 2001, 11, 567-570; Koert et al. Ang. Chem. Int. Ed. 2001, 40(11), 2076-2078; Price et al. Tetrahedron Letters 2004, 45, 5581-5583) and chiral auxiliaries for chemical synthesis (T. K., Chakraborty, K. A. Hussain, G. V. Reddy, Tetrahedron 1995, 51(33), 9179-9190; A. Fadel, A. Khesrani, Tetrahedron: Asymmetry 1998, 9(2), 305-320; K. P. Chiev, S. Roland, P. Mageney, Tetrahedron: Asymmetry 2002, 13(20), 2205-2210; M. P. Bertrand, S. Coantic, L. Feray, R. Nouguier, P. Perfetti, Tetrahedron 2000, 56(24), 3951-3962; J. Lacour et al. J. Org. Chem. 2003, 68(16), 6304-6308; JP 59044345).

Ether formations are one of the standard reactions of organic chemistry which are also carried out on the industrial scale (Organikum, VEB, Berlin 1986, p. 191ff.).

In principle, a distinction is drawn between the acidic and the basic Williamson ether synthesis. In the Williamson O-alkylation, an alkoxide anion is obtained and is reacted with a compound having a nucleofugic leaving group, for example an alkyl halide.

Compounds with a nucleofugic leaving group—i.e. electrophilic reagents—for example alkyl halides, alkyl sulfates, alkylsulfonates, but also benzyl halides or the like, also react, however, readily with nucleophilic amino functions of an organic molecule. When the intention is now to basically etherify an alcohol which also comprises an unprotected or only monosubstituted amino function in the molecule, conditions have to be found under which the reaction of the amino function as far as possible does not occur and the alcohol function is converted fully. Such syntheses are described in the literature differently and with varying success. They are usually the reaction of the amino alcohol with extremely strong bases which react irreversibly to initially form the alkali metal alkoxide ion, which is followed by the reaction with the electrophile (Whitesell et al. J. Org. Chem. 1977, 42, 377; Mayer et al. J. Med. Pharm. Chem. 1961, 3, 409; Meyers et al. J. Org. Chem. 1978, 43, 892, Hu et al. Synth. Commun. 1995, 25(6), 907.). In the case of the use of alkali metal hydrides, the dangerous evolution of hydrogen additionally has to be brought under control on the production scale.

DE 103 44 447 A1 describes the use of alkali metal alkoxides as a deprotonating reagent, the alkali metal alkoxides used being relatively expensive.

Owing to the disadvantages of the prior art processes, there is still a need for regioselective O-alkylation and O-benzylation syntheses of N-unprotected and N-monosubstituted amino alcohols, which can be used advantageously and inexpensively on the industrial scale in particular.

OBJECTIVE

It was therefore an object of the present invention to specify an inexpensive process for regioselective O-alkylation and O-benzylation of N-unprotected and N-monosubstituted amino alcohols, which, in contrast to the prior art, can also be employed advantageously on the industrial scale. In particular, the process should be superior to the prior art processes from the economic and ecological standpoint, and allow the generation of the ethers desired in improved yields and regioselectivities at relatively low costs.

SUBJECT-MATTER OF THE INVENTION

The object is achieved in accordance with the claims by a process for preparing O-alkylated amino alcohols by reacting N-unsubstituted or N-monosubstituted amino alkoxide salts with alkyl halides, the amino alkoxide salts being formed by means of alkali metal or alkaline earth metal hydroxides.

The dependent claims relate to preferred embodiments of the process according to the invention.

The inventive is typically carried out in a solvent. With regard to the selection of the solvent, the person skilled in the art is guided by the product yield, reaction rate, handleability of the alkoxide suspensions formed and the cost of the solvent.

Advantageous solvents are those which can be mixed with the amino alcohol, are chemically inert, i.e. do not react with the amino alcohol, alkali metal hydroxides or alkaline earth metal hydroxides, the water formed or the alkylating or benzylating agent, and typically have a boiling point which is above that of the water which is formed from the alkali metal or alkaline earth metal hydroxides in the deprotonation of the amino alcohol.

Typical solvents suitable for the inventive reaction are aliphatics or aromatics with appropriate boiling points, including mixtures and boiling cuts.

Preference is given to aromatics such as toluene, ortho-xylene, meta-xylene, paraxylene, ethylbenzene, methylethylbenzene, other alkylbenzenes, etc., pp. or mixtures thereof. Particular preference is given to xylene isomer mixtures, since, in the case of the amino alcohols used, the amino alkoxide salts precipitated and formed are obtained in a form which can be handled particularly readily and can be freed of water easily. In addition, simple recycling of the solvent streams is possible.

The N-unsubstituted and N-monosubstituted amino alkoxide salts to be converted are generated by means of alkali metal or alkaline earth metal hydroxides. The alkali metal or alkaline earth metal hydroxides may be used in the reaction as a solid or preferably dissolved in water or suspended in an inert diluent. In this case, the reaction can be completed by distilling off the water which forms.

In a particular embodiment, a further solvent can be used whose boiling point is between the water which forms and the other solvent. This reaction version allows better removal of the water. As the further solvent, preference is given to using alcohols, aliphatic and aromatic ethers and ketones, both cyclic and acyclic.

Particularly preferred those with a number of carbon atoms between 2 and 10, in particular $C_2$-$C_{10}$ alcohols, $C_2$-$C_{10}$ ethers and $C_2$-$C_{10}$ ketones.

In principle, the process according to the invention can be used for a multitude of N-unsubstituted and N-monosubstituted amino alcohols. The amino alcohols used are preferably compounds of the general formula (I) or (II)

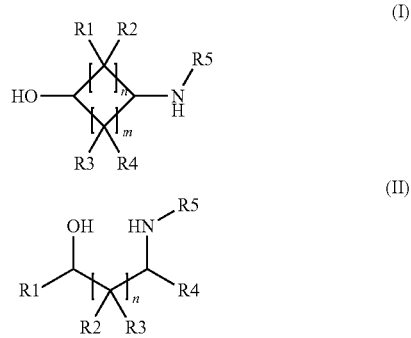

where each independently, n=0, 1, 2, 3, 4 and m=0, 1, 2, 3, 4, and R1, R2, R3, R4 and R5 may each independently be H, substituted and unsubstituted ($C_1$-$C_8$)-alkyl, ($C_3$-$C_8$)-cycloalkyl, ($C_1$-$C_8$)-alkyl-($C_3$-$C_8$)-cycloalkyl, ($C_3$-$C_8$)-cycloalkyl-(($C_1$-$C_8$)-alkyl)1-3, ($C_2$-$C_8$)-alkenyl, ($C_2$-$C_8$)-alkynyl, ($C_6$-$C_{18}$)-aryl, ($C_7$-$C_{19}$)-aralkyl radical, ($C_6$-$C_{18}$)-aryl-(($C_1$-$C_8$)-alkyl) 1-3, ($C_3$-$C_{18}$)-heteroaryl radical, ($C_4$-$C_{19}$)-heteroaralkyl, ($C_3$-$C_{18}$)-heteroaryl radical (($C_1$-$C_8$)-alkyl)1-3.

R5 is preferably H or, in the case of other chiral centers in the molecule, bonded to the nitrogen atom via a chiral carbon atom.

($C_1$-$C_8$)-Alkyl is considered to be: methyl, ethyl, n-propyl, isopropyl, n-butyl, isobutyl, sec-butyl, tert-butyl, pentyl, hexyl, heptyl or octyl including all bonding isomers.

With the exception of methyl, ($C_2$-$C_8$)-alkenyl is understood to mean a ($C_1$-$C_8$)-alkyl radical as described above which has at least one double bond.

With the exception of methyl, ($C_2$-$C_8$)-alkynyl is understood to mean a ($C_1$-$C_8$)-alkyl radical as described above which has at least one triple bond.

($C_3$-$C_8$)-Cycloalkyl is understood to mean cyclopropyl, cyclobutyl, cyclopentyl, cyclohexyl or cycloheptyl radicals, etc. These may have N-, O-containing radicals in the ring, for example 1-, 2-, 3-, 4-piperidyl, 1-, 2-, 3-pyrrolidinyl, 2-, 3-tetrahydrofuryl, 2-, 3-, 4-morpholinyl.

A ($C_6$-$C_{18}$)-aryl radical is understood to mean an aromatic radical having from 6 to 18 carbon atoms. In particular, these include compounds such as phenyl, naphthyl, anthryl, phenanthryl, biphenyl radicals.

A ($C_7$-$C_{19}$)-aralkyl radical is a ($C_6$-$C_{18}$)-aryl radical bonded to the molecule via a ($C_1$-$C_8$)-alkyl radical.

In the context of the invention, a ($C_3$-$C_{18}$)-heteroaryl radical denotes a five-, six- or seven-membered aromatic ring system composed of from 3 to 18 carbon atoms, which has heteroatoms, for example nitrogen, oxygen or sulfur, in the ring. Such heteroaromatics are considered in particular to be radicals such as 1-, 2-, 3-furyl, such as 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acridinyl, quinolinyl, phenanthridinyl, 2-, 4-, 5-, 6-pyrimidinyl. A ($C_4$-$C_{19}$)-heteroaralkyl is understood to mean a heteroaromatic system corresponding to the ($C_7$-$C_{19}$)-aralkyl radical.

The above-defined radicals may be either unsubstituted or mono- or polysubstituted by radicals which either behave inertly under the reaction conditions or which have been masked beforehand by protecting groups. Examples of substituents are OH; $NH_2$, SH, $NO_2$, CN, CO, COOH, F, Cl, Br, I.

In the context of the invention, the term enantiomerically enriched is understood to mean the proportion of one enantiomer in a mixture with its optical antipode in a region of >50% and <100%.

The N-unsubstituted and N-monosubstituted amino alcohols used may be achiral or chiral. They may also be present as racemic, enantiomerically enriched or diastereomerically enriched mixtures. Preference is given to the use of N-unsubstituted or N-monosubstituted 2-aminocycloalkanols or, more preferably, of N-unsubstituted or N-monosubstituted trans-2-aminocycloalkanols. These are obtainable, for example, by ring-opening the corresponding epoxides with ammonia or monosubstituted amines.

Very particular preference is given to the use of N-unsubstituted or N-monosubstituted trans-2-aminocyclopentanol or N-unsubstituted or N-monosubstituted trans-2-aminocyclohexanol.

The alkyl halides employed may be all compounds known to those skilled in the art for this reaction. Preference is given to using ($C_1$-$C_8$)-alkyl chlorides or bromides in the inventive reaction. Very particular preference is given here to primary and secondary alkyl halides, of which those having methyl or ethyl radicals are particularly recommended. Particular preference is given to alkyl chlorides. In addition to the alkyl halides, it is also possible to use alkyl sulfates as alkylating reagents.

The benzyl halides used may preferably be benzyl chloride or benzyl bromide, and the compounds may be mono- or polysubstituted on the aryl radical by common substituents. Particular preference is given to benzyl chloride.

In the inventive reaction, the procedure is preferably to initially charge the substrate and the base in the solvent at temperatures of 20-200° C., preferably 100-150° C., more preferably at the boiling point of the solvent used. Low-boiling solvents, especially the water formed and any second solvent used, can subsequently be removed by distillation. Thereafter, the alkylating agent or benzylating agent is added at temperatures of 20-200° C., preferably 50-150° C., more preferably at the boiling point of the solvent used. The pressure at which the reaction is carried out is not critical per se. For practical reasons, the reaction is preferably carried out at 500-5000 hPa, more preferably at standard pressure.

After the reaction has ended, the mixture can, if appropriate, be allowed to cool and the precipitated inorganic salt can be filtered off or removed in another manner known to those skilled in the art, for example with a centrifuge, cyclotron etc. Alternatively, the inorganic salt formed can also remain in the crude mixture. Thereafter, the product is isolated, for example by distillation.

The distillation can advantageously be effected by a single-stage evaporation, preferably by fractional distillation in one or more, such as 2 or 3, distillation apparatuses. Useful apparatus for the distillation is apparatus customary for this purpose, as described, for example, in: Kirk-Othmer, Encyclopedia of Chemical Technology, 3rd ed., Vol. 7, John Wiley & Sons, New York, 1979, page 870-881, such as sieve tray columns, bubble-cap tray columns, columns with structured packings, columns with random packings, columns with side draw or dividing wall columns.

The distillation can be carried out in batch mode or continuously. Owing to the thermal sensitivity of the substrates, the distillation is preferably carried out at reduced pressure—depending on the corresponding reaction product—of from 1 to 500 hPa, preferably from 5 to 200 hPa.

In the context of the invention, the term diastereomerically enriched is understood to mean the fraction of one diastereomer in a mixture with other diastereomeric isomers in a region of >50% and <100%.

The chiral structures shown relate to all possible diastereomers and enantiomers (R,S), and also mixtures thereof and the racemate.

WORKING EXAMPLES

Example 1

0.2 mol of trans-2-aminocyclohexanol are dissolved in 600 ml of xylene isomer mixture and heated to reflux. 0.2 mol of a 50% sodium hydroxide or potassium hydroxide solution in water is added dropwise to this solution over 15 minutes. In the course of this, the water which has been introduced and which forms is distilled off immediately. After the addition has ended, the water present in the reaction solution is distilled off further until a transition temperature of 140-141° C. is attained. Thereafter, 0.2 mol of benzyl chloride is added dropwise over 30 minutes and the solution is stirred further under reflux for two hours. After aqueous workup, the desired 2-benzyloxycyclohexylamine is obtained in 62% (GC area%) yield in the case of sodium hydroxide, and in 69% (GC area%) yield in the case of potassium hydroxide.

Example 2

0.2 mol of trans-2-aminocyclohexanol are dissolved in 600 ml of xylene isomer mixture and 100 ml of n-butanol and heated to reflux. 0.2 mol of a 50% sodium hydroxide or potassium hydroxide solution in water is added dropwise to this solution over 15 minutes. In the course of this, the water which has been introduced and which forms is distilled off immediately. After the addition has ended, the water present in the reaction solution and then the n-butanol is distilled off until a transition temperature of 140-141° C. is attained. Thereafter, 0.2 mol of benzyl chloride is added dropwise over 30 minutes and the solution is stirred further under reflux for two hours. After aqueous workup, the desired 2-benzyloxycyclohexylamine is obtained in 93% (GC area%) yield in the case of sodium hydroxide, and in 92% (GC area%) yield in the case of potassium hydroxide.

What is claimed is:

1. A process for preparing O-alkylated amino alcohols, which comprises:

reacting N-unsubstituted or N-monosubstituted amino alkoxide salts with alkyl halides, the amino alkoxide salts being formed by alkali metal or alkaline earth metal hydroxides;

wherein the alkyl halide is selected from the group consisting of halides of alkyl, cycloalkyl, alkyl-cycloalkyl, cycloalkyl-alkyl, alkenyl, alkynyl, aryl, aralkyl, and aryl-alkyl; and wherein the reaction is carried out in a solvent.

2. The process according to claim 1, wherein the reaction is carried out in an organic solvent.

3. The process according to claim 2, wherein the alkali metal hydroxide used is potassium hydroxide.

4. The process according to claim 1, wherein xylene is used as the solvent.

5. The process according to claim 4, wherein the alkali metal hydroxide used is potassium hydroxide.

6. The process according to claim 1, wherein the amino alcohol has the following formula (I) or (II):

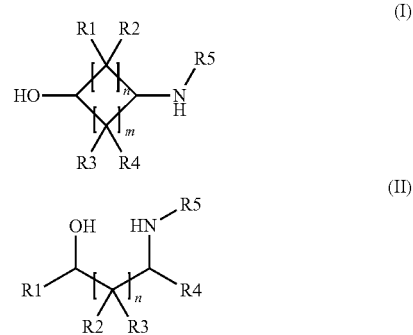

wherein
each independently, n=0, 1, 2, 3, 4 and m=0, 1, 2, 3, 4, and R1, R2, R3, R4 and R5 are each independently H, substituted and unsubstituted $(C_1-C_8)$-alkyl, $(C_3-C_8)$-cycloalkyl, $(C_1-C_8)$-alkyl-$(C_3-C_8)$-cycloalkyl, $(C_3-C_8)$-cycloalkyl-$((C_1-C_8)$-alkyl)1-3, $(C_2-C_8)$-alkenyl, $(C_2-C_8)$-alkynyl, $(C_6-C_{18})$-aryl, $(C_7-C_{19})$-aralkyl radical, $(C_6-C_{18})$-aryl-$((C_1-C_8)$-alkyl)1-3.

7. The process according to claim 6, wherein the substituents in formula (I) have the definition R3, R4, R5=H, n=0, m=4.

8. The process according to claim 7, wherein the alkali metal hydroxide used is potassium hydroxide.

9. The process according to claim 6, wherein the alkali metal hydroxide used is potassium hydroxide.

10. The process according to claim 1, wherein the alkali metal hydroxide used is potassium hydroxide.

* * * * *